US012702784B2

(12) United States Patent
Hansmann et al.

(10) Patent No.: US 12,702,784 B2
(45) Date of Patent: Aug. 11, 2026

(54) ARRANGEMENT AND PROCESS FOR SUPPLYING A PATIENT-SIDE COUPLING UNIT WITH A GAS MIXTURE

(71) Applicant: Drägerwerk AG & Co. KGaA, Lübeck (DE)

(72) Inventors: Hans-Ullrich Hansmann, Lübeck (DE); Oliver Garbrecht, Lübeck (DE); Hendrik Fischer, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 838 days.

(21) Appl. No.: 18/074,656

(22) Filed: Dec. 5, 2022

(65) Prior Publication Data

US 2023/0181864 A1 Jun. 15, 2023

(30) Foreign Application Priority Data

Dec. 14, 2021 (DE) .................... 10 2021 132 928.0

(51) Int. Cl.
*A61M 16/12* (2006.01)
*A61M 16/00* (2006.01)
(Continued)

(52) U.S. Cl.
CPC ...... *A61M 16/125* (2014.02); *A61M 16/0081* (2014.02); *A61M 16/1005* (2014.02); *A61M 2016/0027* (2013.01); *A61M 16/0066* (2013.01); *A61M 16/204* (2014.02); *A61M 16/208* (2013.01); *A61M 2202/0208* (2013.01);
(Continued)

(58) Field of Classification Search
CPC .............. A61M 16/00; A61M 16/0057; A61M 16/0066; A61M 16/0081; A61M 16/01; A61M 16/024; A61M 16/08; A61M 16/0816; A61M 16/0883; A61M 16/1005; A61M 16/12; A61M 16/122; A61M 16/125; A61M 16/204; A61M 16/208;
(Continued)

(56) References Cited

U.S. PATENT DOCUMENTS 3,664,361 A * 5/1972 Bartels .................... A62B 7/12 137/98
3,762,427 A 10/1973 Mollering
(Continued)

FOREIGN PATENT DOCUMENTS

EP 2425869 A1 3/2012
WO 2021203050 A1 10/2021

*Primary Examiner* — Joseph D. Boecker
(74) *Attorney, Agent, or Firm* — McGlew and Tuttle, P.C.

(57) ABSTRACT

An arrangement and process supply a patient-side coupling unit with a gas mixture including a first gas component and a second gas component. A first duct (K.1) directs the first gas component from a first source (E) to a mixing point (8). The second gas component flows from a second source (25) to a buffer reservoir (5) and from the buffer reservoir (5) through a second duct (K.2) to the mixing point (8). The gas mixture flows from the mixing point (8) through an inspiration duct (K.30) to the patient-side coupling unit. A pneumatic control line (28) provides a control fluid connection between the first duct (K.1) and the buffer reservoir (5). A pressure balancing is effected between the pressure inside (In.O2, In.k1) the buffer reservoir (5), the pressure in the first duct (K.1), and the pressure in the second duct (K.2).

15 Claims, 6 Drawing Sheets

(51) Int. Cl.
*A61M 16/10* (2006.01)
*A61M 16/20* (2006.01)

(52) U.S. Cl.
CPC ............... *A61M 2205/3334* (2013.01); *A61M 2205/3355* (2013.01)

(58) Field of Classification Search
CPC .. A61M 2016/0027; A61M 2205/3334; A61M 2205/3355
See application file for complete search history.

(56) References Cited

U.S. PATENT DOCUMENTS 4,549,563 A * 10/1985 Monnier ............. A61M 16/104 128/203.14
2012/0192956 A1 * 8/2012 Weiszl .................. A61M 16/20 137/88

* cited by examiner

Pt
9
100
3
30
K.1
4.1
4.2
8
Air + O2
K.30
6.1
6.2
K.4
O2
18
K.2
28
16.1
16.2
K.3
A
V.1
V.2
V.3
V.4
28.1
1
2
23
E
Air
5
In.O2
7
10
In.K1
26
27
25
29
21
W
20

Pt
9
100
3
30
K.1
Air + O2
K.30
4.2
8
4.1
6.1
6.2
K.2
O2
28
V.1
2
32
23
E
Air
5
7
10
In.O2
In.K1
26
27
25

$O_2$
28
100
28
K.2
7
5
10
In.$O_2$
In.K1
26
$O_2$ $O_2$
28
100
28
K.2
7
5
10
In.K1
In.$O_2$
26
$O_2$ 5
28
28
100
K.2
7.1
10
In.K1
In.O2
26
O2
O2

ARRANGEMENT AND PROCESS FOR SUPPLYING A PATIENT-SIDE COUPLING UNIT WITH A GAS MIXTURE

CROSS REFERENCE TO RELATED APPLICATIONS

This application claims the benefit of priority under 35 U.S.C. § 119 of German Application 10 2021 132 928.0, filed Dec. 14, 2021, the entire contents of which are incorporated herein by reference.

TECHNICAL FIELD

The invention relates to an arrangement and process for supplying a gas mixture to a patient-side coupling unit.

The invention can be used, for example, for artificial ventilation of a patient. A patient-side coupling unit is arranged in or on or at the patient's body, the patient-side coupling unit being a breathing mask, a catheter or a tube, e.g. to artificially ventilate the patient, a gas mixture is delivered to the patient-side coupling unit. This gas mixture comprises oxygen and, in one embodiment, additionally at least one anesthetic.

Preferably, a ventilator performs a sequence of ventilation strokes and delivers a quantity of the gas mixture to the patient-side coupling unit in each ventilation stroke.

BACKGROUND

It is possible that breathing air is used as the gas mixture. It is often desired that the percentage of oxygen in the gas mixture delivered to the patient-side coupling unit is greater than the percentage of oxygen in the breathing air. To achieve this goal, a gas mixture comprising breathing air and pure oxygen is generated. The invention can be applied to generate and deliver such a gas mixture to the patient-side coupling unit.

The ventilator 14 according to EP 2 425 869 A1 comprises a mixing device and a ventilation part. A medical gas, for example, oxygen or an anesthetic, is mixed with air in the mixing device. The medical gas is fed via a gas inlet B and is fed via a gas line 10. The air is fed via an air inlet A and is fed via an air line 11. A reducing valve 6, a safety valve 7, a controllable proportional valve 8 and a flow meter 9 are arranged in the gas line 10. A blower 1 and a nonreturn valve 2 are arranged in the air line 11. The ventilation part guides the gas mixture to a patient via a breathing gas line 12 as breathing gas. A flow sensor 3, a controllable proportional valve 4 and a pressure sensor 5 are arranged in the breathing gas line 12. A control unit 13 receives signals from the sensors 9, 3 and is capable of controlling all controllable valves 8, 4.

SUMMARY

A basic object of the present invention is to provide an arrangement and a process which are capable of supplying a patient-side coupling unit with a gas mixture comprising at least two gas components, the time course of the pressure of the gas mixture supplied or of the volume flow of the gas mixture to the patient-side coupling unit can be regulated in a relatively reliable manner.

The invention is accomplished by an arrangement having features according to the invention and by a process having the features according to the invention. Advantageous embodiments are presented by this disclosure. Advantageous embodiments of the arrangement are, as far as useful, also advantageous embodiments of the process according to the invention and vice versa.

The arrangement and process according to the invention are able to supply a patient-side coupling unit with a gas mixture. The gas mixture comprises a first gas component, for example breathing air, and a second gas component, for example pure oxygen. The gas mixture may comprise a third gas component, for example an anesthetic.

The patient-side coupling unit is connected or at least temporarily connectable to a patient. In particular, the patient-side coupling unit is arrangeable on the patient's face or insertable into the patient's body.

In the following, the term "duct" is used. A duct is understood to be a component which is capable of directing a fluid, in particular a gas or gas mixture, along a predetermined trajectory and ideally prevents the fluid from leaving this trajectory. A hose and a tube are examples of a duct.

In the following it is also mentioned that a "fluid connection" is established between two components. This is understood to mean that a fluid can flow from one component to the other, ideally without escaping into the environment. It is possible that the two components are directly connected to each other. It is also possible that a gap occurs between the two components and a fluid guiding unit, for example a hose, connects the two components. It is possible that a fluid flows temporarily from the first component through the fluid connection to the second component, and at times vice versa from the second component through the fluid connection to the first component. The fluid connection can be established permanently or only temporarily.

In the context of the invention, a "buffer reservoir" is understood to be a component which can receive a quantity of a fluid in its interior and release it again. It is possible that the volume of the buffer reservoir changes, with the buffer reservoir increasing when the gas is received and decreasing when the gas is released. It is also possible that the volume of the buffer reservoir is constant over time and the buffer reservoir temporarily stores a fluid, in particular a gas, under overpressure.

The buffer reservoir comprises at least one chamber in its interior, optionally several chambers. The chamber or each chamber is capable of receiving and discharging a fluid. If the buffer reservoir comprises at least two chambers, these two chambers are preferably separated from each other in a fluid-tight manner and can receive different fluids.

Furthermore, the term "source" is used hereinafter. In the context of the invention, a source is capable of providing a fluid, in particular a gas component. A source is in particular a stationary supply connection or a mobile source, for example a container with the fluid, in particular a compressed air cylinder. It is possible that two different types of sources are used, in particular a stationary source and a mobile source.

The supply arrangement according to the invention comprises a first duct with a supply connection element. A fluid connection between the supply connection element and a first source is established or can be established at least temporarily. This first source is a source of the first gas component.

The supply arrangement according to the invention further comprises a buffer reservoir. A supply chamber is arranged inside the buffer reservoir. A fluid connection is established or can be established permanently or at least temporarily between the supply chamber and a second source. This second source is a source of the second gas component. The second gas component is chemically different from the first gas component. It is possible that both gas components include the same component, for example both comprise oxygen. The supply chamber is capable of receiving and releasing an amount of the second gas component.

Furthermore, the supply arrangement according to the invention comprises a second duct. A supply fluid connection is established or can be established at least temporarily between the supply chamber and the second duct.

The first duct is adapted to direct the first gas component from the supply connection element to a mixing point of the supply arrangement. The second duct is adapted to direct the second gas component from the buffer reservoir to this mixing point. Thus, the gas mixture comprising the first gas component and the second gas component can be formed at the mixing point. It is also possible that the gas mixture is formed by itself at the mixing point.

The supply arrangement according to the invention further comprises an inspiration duct. This inspiration duct leads from the mixing point to the patient-side coupling unit and is capable of directing a gas mixture, which has been formed in the mixing point, from the mixing point to the patient-side coupling unit.

Thus, according to the invention, the first duct and the second duct guide into the mixing point, and the inspiration duct starts in the mixing point. In the simplest case, the mixing point is a purely mechanical component connecting these three ducts in the manner of a Y-piece.

Furthermore, the supply arrangement according to the invention comprises a pneumatic control line. This pneumatic control line establishes a control fluid connection between the first duct and the buffer reservoir. A fluid can thus flow from the first duct through the pneumatic control line to the buffer reservoir, and optionally vice versa from the buffer reservoir through the pneumatic control line to the first duct. The term “pneumatic control line” distinguishes the control line according to the invention from a data line and from an electrical line.

The buffer reservoir, the supply fluid connection and the control fluid connection achieve the following effect with cooperation: Between the pressure in the supply chamber, the pressure in the first duct and the pressure in the second duct a pressure balancing is effected, even if the pressure downstream of the mixing point and therefore also the pressure in the first duct and/or the pressure in the second duct vary over time. With artificial ventilation of a patient, the respective pressure usually varies in at least one duct.

The process according to the invention is carried out using such a connection arrangement. The process comprises the following steps:

- The first gas component is provided at the supply connection element, for example by being guided to the supply connection element.
- The first duct directs the first gas component from the supply connection element to the mixing point.
- The second gas component is directed to the buffer reservoir.
- The second gas component flows into the supply chamber.
- The second gas component is directed out of the supply chamber and through the supply fluid connection into the second duct.
- The second duct directs the second gas component from the buffer reservoir to the mixing point.
- The gas mixture is generated at the mixing point from the two gas components or is formed by itself at the mixing point.
- The gas mixture is directed from the mixing point through the inspiration duct to the patient-side coupling unit.

The pneumatic control line provides a control fluid connection between the first duct and the buffer reservoir.

A pressure balancing between the pressure in the supply chamber, the pressure in the first duct and the pressure in the second duct is automatically effected.

The invention enables a gas mixture comprising at least two gas components to be delivered to the patient-side coupling unit, thereby providing the gas mixture at or in the patient-side coupling unit for artificial ventilation of a patient. Because the supply arrangement is configured to comprise the gas mixture of at least two gas components, the invention in many cases enables a gas mixture to be provided which is tailored to the artificial ventilation currently required by the patient. In particular, pure oxygen can act as the second gas component, and the percentage of oxygen in the gas mixture can be adjusted and changed as required. An anesthetic agent may also function as the second gas component.

According to the invention, a buffer reservoir is arranged between the second source and the second duct. With use of the supply arrangement, the second gas component flows from the second source to the buffer reservoir, into and out of the supply chamber and further from the buffer reservoir into the second duct. Thanks to the buffer reservoir, the control fluid connection and the supply fluid connection, pressure is automatically balanced between the pressure in the first duct and the pressure in the second duct. As a result, the pressure in the first duct and in the second duct are approximately the same, at least with a certain time delay, even if the pressure in the first duct and/or the volume flow through the first duct vary with time.

These two coinciding pressures in the two ducts make it easier to mix the two gas components and to automatically control the volume flow and/or the pressure of the gas mixture downstream of the mixing point. The control objective with this optional control is that the actual time course of the volume flow or pressure in the inspiration duct follows a predetermined target time course. This closed-loop control in turn facilitates artificial ventilation of the patient, particularly in the case of supportive artificial ventilation which supports the patient’s own respiratory activity. In particular, the control makes it easier to synchronize the ventilation strokes of a ventilator with the patient’s own respiratory activity.

According to the invention, the pneumatic control line establishes a control fluid connection between the first duct and the buffer reservoir. This causes a pressure balancing between the pressure in the first duct and the pressure inside the buffer reservoir. The effected pressure balancing also acts on the supply chamber, preferably from the outside. Thanks to the supply fluid connection, a pressure balancing is effected between the pressure in the supply chamber and the pressure in the second duct. This also causes a pressure balancing between the pressure in the first duct and the pressure in the second duct.

The buffer reservoir with the supply chamber pneumatically decouples the second source from the second duct, to a large extent independently of the pressure and volume flow rate at which the second source provides the second gas component. The second source can provide the second gas component with a time-constant or time-varying pressure and volume flow. Therefore, the buffer reservoir avoids the need to control the pressure or volume flow at which the second source provides the second gas component. This facilitates using an existing or currently available second source to provide the gas mixture at the patient-side coupling unit. This effect is particularly advantageous when the second source is a mobile source which is difficult or impossible to control. The effect is often also advantageous when a stationary supply network supplies various supply arrangements according to the invention with the second gas component.

Thanks to the pneumatic control line, it is possible, but not necessary, to configure the buffer reservoir in such a way that a control unit automatically controls the buffer reservoir depending on the measured values of a pressure sensor. Rather, in many cases it is possible for the buffer reservoir to be configured as a purely mechanical component. Therefore, the buffer reservoir does not require any electrical power or data connection. In many cases, such a buffer reservoir is mechanically more stable and/or more robust against environmental influences than an electronically controllable buffer reservoir.

It is possible for a signal processing control unit (control unit) to receive and to process measured values from a pressure sensor, whereby this pressure sensor measures an indicator for the pressure in the first duct. According to one embodiment, the control unit controls the buffer reservoir depending on measured values from the pressure sensor, the target in the control being that the pressure inside the buffer reservoir, in particular in the supply chamber, follows the pressure in the first duct. Thanks to the supply fluid connection, the pressure in the second duct then also follows the pressure in the first duct.

It is also possible that the or a pressure sensor measures the pressure downstream of the mixing point, i.e. in the inspiration duct. Again, according to one embodiment, the control unit controls the buffer reservoir depending on the measured values of the pressure sensor. The target in this control is that the pressure inside the buffer reservoir follows the pressure in the inspiration duct. Thanks to the control fluid connection and the supply fluid connection, the pressure in the first duct and the pressure in the second duct also follow the pressure in the inspiration duct.

Instead of a pressure sensor or in addition to the pressure sensor, a sensor for the volume flow through the respective duct can also be used.

In one embodiment, the buffer reservoir comprises the supply chamber as the only chamber. The supply chamber is in fluid communication with the second source. The buffer reservoir is in fluid communication with the first duct via the pneumatic control line. In one embodiment, the buffer reservoir further comprises an actuator. The control fluid connection connects this actuator to the pneumatic control line. Depending on the pressure in the control line, the actuator is adapted to cause the pressure in the supply chamber to follow the pressure in the first duct. For example, the actuator is able to change the volume of the supply chamber. The actuator may be configured as a purely mechanical and hydraulic actuator, i.e. not requiring any electrical energy.

In a preferred embodiment, the buffer reservoir comprises a housing and a flexible fluid-tight separating element. Preferably, the housing is rigid. The separating element is arranged inside the housing and is preferably fixed to the inside of the housing. The separating element divides the interior of the housing in a fluid-tight manner into two different chambers, namely the supply chamber and a control chamber. Thanks to the separating element, a fluid is prevented from passing from one chamber to the other chamber.

It is possible that the two chambers together take the entire interior of the housing. It is also possible that part of the buffer reservoir neither belongs to the supply chamber nor to the control chamber. The term "fluid-tight" is not necessarily to be understood in absolute terms, but may include the possibility of fluid passing through unavoidable leaks from one chamber to the other.

The fluid connection between the buffer reservoir and the second source connects at least temporarily the supply chamber inside the housing to the second source, that is, to the source of the second gas component. The supply fluid connection between the buffer reservoir and the second duct connects the supply chamber to the second duct. Thanks to this embodiment, the second source is in fluid communication with the second duct, this fluid communication passing through the supply chamber. The supply fluid connection causes a pressure balancing between the pressure in the supply chamber and the pressure in the second duct. Because the separating element fluidly separates the two chambers, the second gas component is prevented from passing through the pneumatic control line and into the first duct.

The pneumatic control line and therefore the control fluid connection connect the control chamber inside the housing to the first duct. Thereby, a fluid connection is established between the first duct and the control chamber, this fluid connection being part of the control fluid connection according to the invention. The pneumatic control line effects a pressure balancing between the pressure in the first duct and the pressure in the control chamber.

According to one variation of this embodiment, the separating element is flexible. According to another variation of this embodiment, the separating element is rigid and arranged movably relative to the housing, for example slidably or pivotably mounted. For example, the separating element is a slidably mounted rigid plate.

In both variations, at least one area of the separating element can change its position relative to the housing of the buffer reservoir. This change is caused in particular by a difference between the pressures in the two chambers and reduces the pressure difference. Ideally, the flexible separating element completely eliminates a pressure difference between the two chambers.

Because the separating element inside the housing is flexible and/or movable, a pressure balancing between the pressure in the supply chamber and the pressure in the control chamber is established by itself. After the pressure in one chamber has changed, it usually takes some time for the pressure in the other chamber to change accordingly. This pressure balancing takes place automatically without the need for any external control or intervention. Rather, the separating element can be a passive mechanical component. This pressure balancing causes a pressure balancing between the pressure in the first duct and the pressure in the second duct via the impact chain described above.

According to the invention, the pneumatic control line connects the buffer reservoir to the first duct. This feature can be combined with an embodiment in which the buffer reservoir is controlled electronically. This combination creates redundancy and, in some cases, allows the pressures in the two chambers to balance even faster.

Preferably, the supply chamber is large enough to hold and release at least one tidal volume. As is known, the tidal volume is the volume that a patient inhales during a single breath. Thanks to this embodiment, the supply chamber is able to provide, at any desired mixing ratio, a quantity of the second gas component sufficient for a single ventilation stroke.

In one configuration of the embodiment with the two chambers inside the buffer reservoir, the separating element is configured as a flexible fluid-tight bag or comprises a flexible fluid-tight bag. A gap occurs between the housing and the bag, at least in some areas, the gap forming an interior space. This interior space at least partially encloses the bag. The housing surrounds and protects the bag. The separating element separates the interior space from the interior of the bag. The interior of the bag forms a chamber, and the interior space in the housing around the bag forms another chamber.

In a first alternative of this embodiment, the control chamber is formed in the interior space between the housing and the bag. The pneumatic control line provides the control fluid communication connecting the interior space between the bag and the housing to the first duct. The supply chamber is disposed within the interior of the bag and is enclosed by the bag. The supply fluid connection connects the interior of the bag to the second duct.

In a second alternative, the control chamber is formed inside the bag. The pneumatic control line provides the control fluid connection between the interior of the bag and the first duct. The supply chamber is formed in the interior between the housing and the bag. The supply fluid connection connects this interior space to the second duct.

Both alternatives of the embodiment with the bag make it possible in many cases to provide a mechanically particularly robust buffer reservoir. If the buffer reservoir is cuboidal, it is sufficient in many cases to connect the bag to a wall of this cuboid and to provide an opening in this wall through which the supply fluid connection is directed.

In order for a pressure balancing to take place between the two ducts, the second source must provide neither too large a quantity nor too small a quantity of the second gas component. Otherwise, the buffer reservoir will no longer be able to provide the desired pressure balancing. Various embodiments are possible for monitoring the buffer reservoir and triggering an automatic change or at least an alarm if required.

In one embodiment, the housing is transparent, or the housing has a viewing window. A user can visually monitor from the outside the buffer reservoir and in particular the position of the separating element. In particular, it is possible to detect the undesirable situation where the actual position of the separating element deviates greatly from a position that occurs when the pressure between the two chambers is balanced. If the separating element comprises a bag, it is possible to visually detect both the undesirable event that the bag is strongly compressed (too low pressure in the bag/too large pressure in the interior space between the bag and the housing) and the undesirable event that the bag is pressed against the inner wall of the housing (too large pressure in the bag/too low pressure in the interior space).

Another implementation eliminates the need to visually monitor the buffer reservoir. In one implementation of the embodiment with the two chambers inside the buffer reservoir, the supply arrangement comprises a sensor arrangement. In one implementation this sensor arrangement is able to measure an indicator for a pressure difference, namely the difference between the pressure in the supply chamber and the pressure in the control chamber. If the measured pressure difference is outside a predetermined range around zero for a sufficiently long period of time, a message is generated and preferably output in a form that can be perceived by a human. In another embodiment, the sensor arrangement is capable of measuring an indicator of the volume of the bag. For example, the sensor arrangement detects the undesirable event of the bag being pressed against the housing from the inside, indicating that the volume of the bag is too large.

The embodiment with the transparent housing or the viewing window can be combined with the embodiment comprising the sensor arrangement.

One possible solution is to at least temporarily change the pressure at which the second source is capable of providing the second gas component.

According to the invention, the supply arrangement is capable of generating a gas mixture comprising a first gas component and a second gas component. The first gas component is provided by the first source, and the second gas component is provided by the second source. In one embodiment, the supply arrangement is capable of generating a gas mixture further comprising a third gas component, for example an anesthetic. A third source provides the third gas component.

In another embodiment, both the second source and another source are capable of providing the second gas component. This provides redundancy. Preferably, the further source provides the second gas component at a higher pressure than the second source. For example, the second source is a mobile source, in particular an oxygen generator, and the further source is a stationary supply port or comprises a pressurized cylinder. In this application, the supply arrangement preferably further comprises a pneumatic pressure reducer having an upstream pressure inlet and a downstream pressure outlet.

Furthermore, the supply arrangement comprises a third duct for directing the second gas component. In one alternative, this third duct leads to the mixing point to which the first duct and the second duct also lead. In another alternative, the third duct leads to a further mixing point which is in fluid communication with the mixing point and may be located upstream or downstream of the mixing point. The inspiration duct leads from the mixing point or the further mixing point to the patient-side coupling unit.

A fluid connection is established or can be established between the upstream pressure inlet of the pressure reducer and the further source, so that the second gas component can be fed from the further source into the pressure reducer. The downstream pressure outlet of the pressure reducer is connected to the third duct, so that the pressure reducer can feed the second gas component into the third duct.

The pressure reducer provides the second gas component at its downstream pressure outlet. At least as a rule, the pressure at the downstream pressure outlet is less than the pressure at the upstream pressure inlet, i.e, the pressure reducer reduces the pressure. The pressure reducer is configured such that providing the second gas component has the following effect: The time course of the pressure at the downstream pressure outlet follows the time course of the pressure at the supply connection element.

It is possible that a pressure sensor measures the pressure in the first duct and a signal processing control unit controls the pressure reducer depending on a signal from the pressure sensor for the first duct.

It is possible that a signal processing controller (control unit) electronically controls the pressure reducer so that the pressure at which the pressure reducer provides the second gas component at the downstream pressure outlet follows the pressure in the first duct.

In another embodiment with the pressure reducer, the pressure reducer additionally comprises a control pressure input. The supply arrangement comprises a further pneumatic control line. The further pneumatic control line provides a fluid connection between the first duct and the control pressure input. The further pneumatic control line eliminates the need to electronically control the pressure reducer. Instead, it is possible to configure the pressure reducer as a purely mechanical and pneumatic component. The two implementation forms, with the electronic control and the additional pneumatic control line, can also be combined.

The invention further relates to a system capable of supplying a gas mixture to a patient-side coupling unit. This gas mixture comprises a first gas component and a second gas component. The supply system includes a first source, a second source and a supply arrangement according to the invention. The first source provides the first gas component, and the second source provides the second gas component. A fluid connection is established at least temporarily between the supply connection element of the first duct of the supply arrangement and the first source. A fluid connection is also established at least intermittently between the supply chamber in the buffer reservoir of the supply arrangement and the second source.

The advantages of the supply arrangement according to the invention that have been described also apply to this supply system. Possible advantageous embodiments of the supply arrangement according to the invention are also advantages of the supply system.

In one embodiment, the supply system additionally comprises a further source which is also capable of providing the second gas component, preferably at a higher pressure than the second source. The supply arrangement additionally comprises a pressure reducer. An upstream pressure inlet of the pressure reducer is in fluid communication with the further source, and a downstream pressure outlet of the pressure reducer is in fluid communication with the second duct. The pressure at the downstream pressure outlet tracks the pressure in the first duct.

Furthermore, the invention relates to a system capable of artificially ventilating a patient. This ventilation system comprises the above-mentioned patient-side coupling unit, a fluid delivery unit and a supply arrangement or supply system according to the invention. The fluid delivery unit is adapted to deliver a gas mixture to the patient-side coupling unit, said gas mixture having been generated by the supply arrangement or supply system. The fluid delivery unit may be arranged upstream or downstream of the mixing point.

In the following, the invention is described with reference to exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
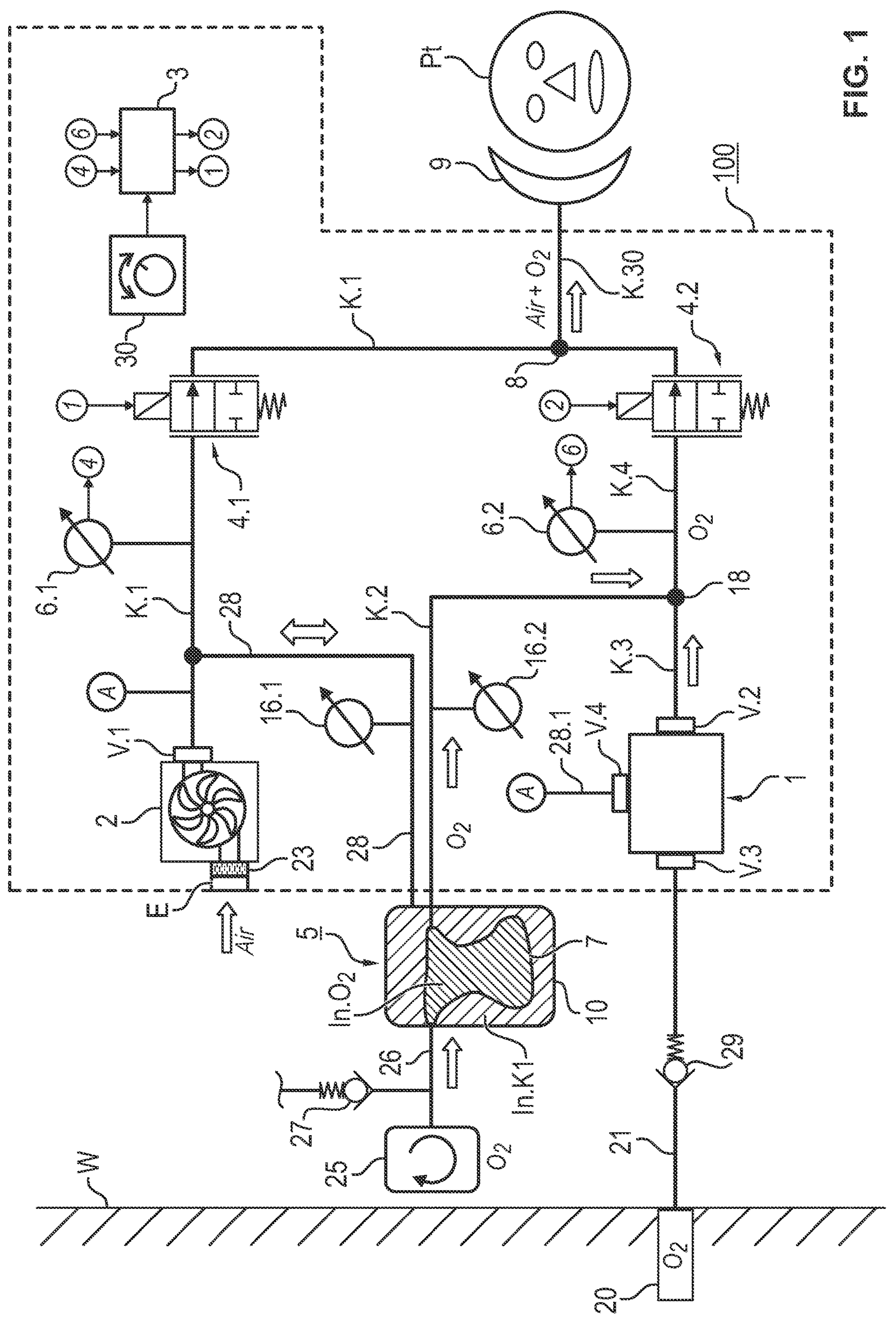
FIG. 1 is a schematic view showing a patient-side coupling unit supplied with a gas mixture of breathing air and pure oxygen, with two different sources providing the pure oxygen at different pressures.

Referring to the drawings, in an exemplary embodiment, the invention is used to provide artificial ventilation to a patient Pt. A patient-side coupling unit 9, for example a breathing mask or a tube or a catheter, is attached at or in the body of the patient Pt.

A ventilator 100, shown only schematically, performs a sequence of ventilation strokes and with each ventilation stroke delivers a gas mixture to the patient-side coupling unit 9 and thus to the patient Pt. The supply arrangement according to the invention is part of the ventilator 100. The gas mixture contains a percentage (vol-%) of oxygen, a user having predetermined a setpoint value for this percentage. This percentage of oxygen may be above the percentage of oxygen in the breathing air. In order to increase the percentage of oxygen relative to the breathing air, a gas mixture of breathing air and pure oxygen is generated in the embodiment example. The gas mixture may additionally contain an anesthetic such that the patient Pt is sedated or anesthetized.

A user specifies a desired oxygen content in the gas mixture. For example, the user manually sets the oxygen level on a rotary knob 30.

FIG. 1 shows a first embodiment of an arrangement to generate this gas mixture with a higher oxygen content and to deliver it to the coupling unit 9 on the patient side. A first duct K.1 provides the breathing air. A second duct K.2 and a third duct K.3 provide pure oxygen. The second duct K.2 and the third duct K.3 open into an oxygen mixing point 18. A fourth duct K.4, which also directs pure oxygen, starts at the mixing point 18. The term "duct" refers to a fluid guiding unit capable of directing a fluid, e.g. oxygen along a trajectory.

The first duct K.1 and the fourth duct K.4 open into a mixing point 8. From this mixing point 8, an inspiration duct K.30, for example a tube for inhalation and optionally a two-lumen tube with an additional tube for exhalation, leads to the patient-side coupling unit 9. This inspiration duct K.30 directs the mixture of air and pure oxygen to the patient-side coupling unit 9.

It is also possible that the gas mixture contains a third gas component, for example an anesthetic. In this embodiment, a third duct (not shown) directs the third gas component to the mixing point 8.

A blower 2 or pump or other fluid delivery unit of the ventilator 100 draws in ambient air through an inlet E of the fluid delivery unit 2 and feeds the drawn-in air into the first duct K.1. A filter 23 is arranged between the inlet E and the blower unit 2. In the application according to FIG. 1, the inlet E acts as the source of the first gas component.

A supply connection element V.1 of the first duct K.1 is connected to a supply output of the blower 2. The pressure in the first duct K.1 ideally follows a predetermined time course, for example is constant over time. The pressure in the first duct K.1 is preferably always above the maximum ventilation pressure, i.e. above the maximum pressure at which the gas mixture is directed to the coupling unit 9 on the patient side and further into the lungs of the patient Pt, and is preferably between 20 mbar and 100 mbar.

Figure 3:
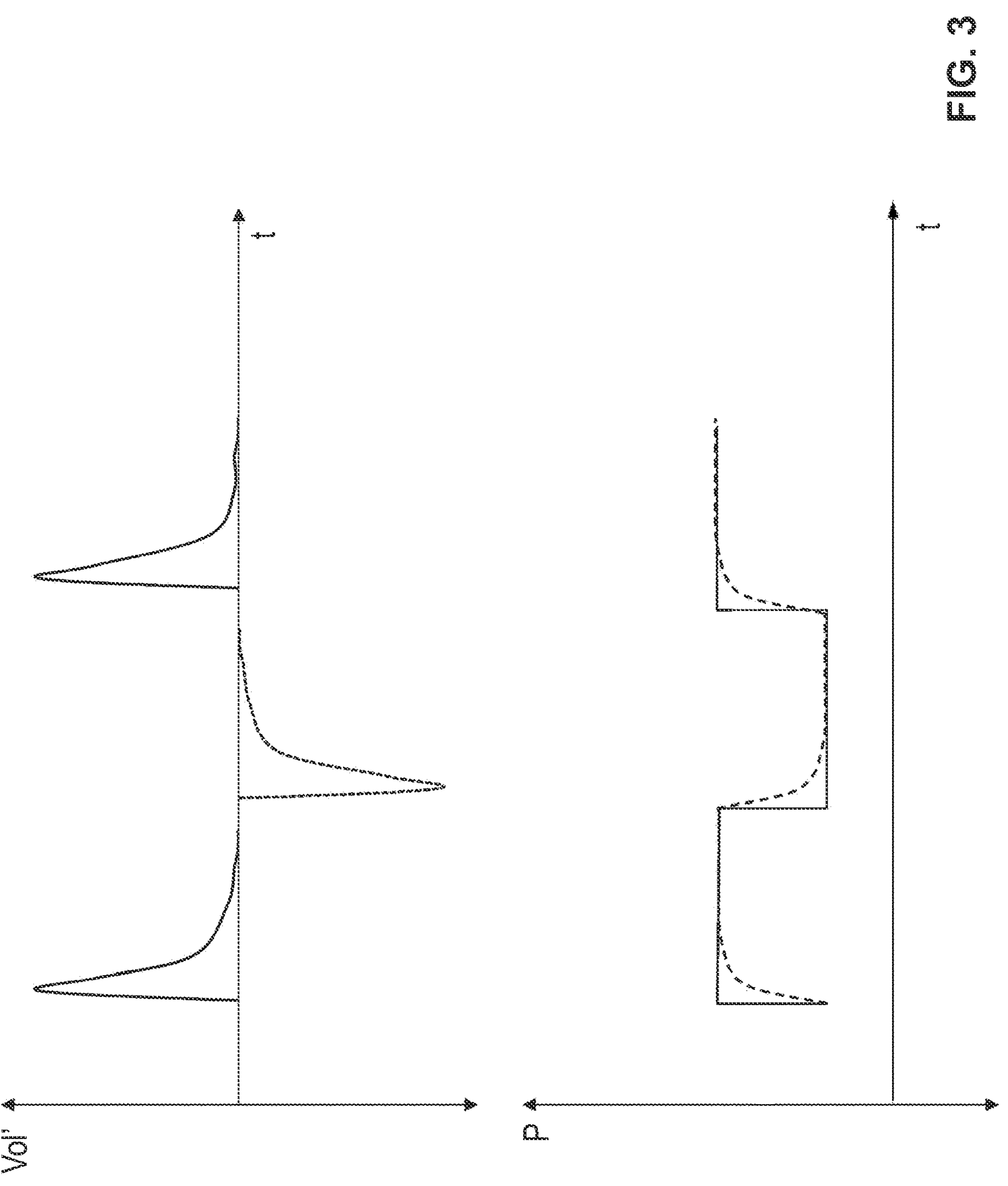
FIG. 3 is a view with graphs showing an exemplary time course of the volume flow and the pressure in the inspiration duct.

The volume flow, i.e, the flow of gas per unit of time, through the inspiration duct K.30 to the coupling unit 9 on the patient's side should follow a predetermined time course. FIG. 3 shows an exemplary required time course of the volume flow (Vol') at the top and an exemplary required time course of the pressure (P) at the bottom. Values above the x-axis indicate a flow of the gas mixture towards the patient Pt (inspiration), values below indicate a flow away from the patient Pt (exhalation).

A signal-processing control unit 3 performs closed-loop control, whereby the actual volume flow Vol' is the controlled variable and the specified time course of the volume flow is the gain variable. The actual volume flow Vol' to the patient-side coupling unit 9 is the sum of the volume flows through the two ducts K.1 and K.4, which lead into the mixing point 8.

A volume flow sensor 6.1 provides a measure of the actual volume flow in the first duct K.1. For example, the volume flow sensor 6.1 measures a pressure difference between two measurement points spaced apart in the direction of flow in the first duct K.1. The control unit 3 controls a proportional valve 4.1, thereby changing the volume flow through the first duct K.1 downstream from the proportional valve 4.1 to the mixing point 8 as required.

A volume flow sensor 6.2 and a proportional valve 4.2 are arranged in the fourth duct K.4. These components function in the same way as the corresponding components in the first duct K.1. The control unit 3 controls the proportional valve 4.2 with the control objective that the actual volume flow through the fourth duct K.4 follows a predetermined time course.

As already explained, a gas mixture is directed from the mixing point 8 to the coupling unit 9 on the patient side. The actual volumetric flow Vol' of this gas mixture downstream of the mixing point 8 is to follow a predetermined time course.

Furthermore, a percentage of oxygen in the gas mixture is predetermined, preferably predetermined as Vol-%. This percentage of oxygen may be constant over time or variable over time. The two proportional valves 4.1 and 4.2 can each change a volume flow, but not an oxygen percentage.

Pure oxygen flows through the fourth duct K.4, breathing air through the first duct K.1. The required percentage of oxygen in the gas mixture and the known percentage of oxygen in air result in a required target ratio between the two volume flows through the two ducts K.1 and K.4. The specified time course of the volume flow to the patient-side coupling unit 9 and the target ratio of the volume flows result in a target course of the volume flow in the first duct K.1 and a target course of the volume flow in the fourth duct K.4 and in a setpoint course of the volume flow in the fourth duct K.4. The control unit 3 or a higher-level control unit calculates these two setpoint courses for the two ducts K.1 and K.4, and the control unit 3 controls the two proportional valves 4.1 and 4.2 as a function of these two setpoint courses. The control unit 3 thus performs two controls of the volume flow, namely one in the first duct K.1 and one in the fourth duct K.4.

The second duct K.2 supplies pure oxygen at a lower pressure than the third duct K.3. In the shown embodiment example, the second duct K.2 is connected via a connecting line 26 to a schematically shown and preferably mobile second source 25. A pressure relief valve 27 opens when the pressure in the connecting line 26 is above a predetermined barrier of, for example, 100 mbar, thereby limiting the pressure in the connecting line 26.

In one embodiment, the second source 25 receives breathing air from the environment and absorbs a greater portion of the nitrogen from the breathing air through multiple pressure changes. Here, the ambient air is stored under elevated pressure in a first tank containing zeolites. There a part of the nitrogen is absorbed. The compressed gas with a reduced percentage of nitrogen is fed into a subsequent second tank. In the first tank, the pressure decreases, the air expands, and the nitrogen is desorbed and purged as waste gas. This process is repeated several times until a sufficiently high oxygen concentration is reached. A source operating in this way can deliver a gas mixture with a maximum of 95% oxygen by volume. Noble gases in the ambient air remain in this gas mixture. The oxygen content of the gas mixture from the second source is taken into account when calculating the target volume flows.

It is also possible that the mobile source 25 contains chemicals, such as bulk or solid materials, that undergo an exothermic chemical reaction in response to activation, such as contact with moisture. In this reaction, the source 25 provides oxygen. The substance is, for example, sodium chlorate. For example, the source comprises at least one chlorate candle. For example, the mobile source 25 undergoes the chemical reaction 2 $NaClO_3 \rightarrow 2\ NaCl + 3\ O_2$. Typically, such a mobile source 25 is capable of providing oxygen at a pressure of at most 500 mbar.

The third duct K.3 receives pure oxygen (O2) from a supply line 21 which is in communication with a supply port 20. In the example shown, this supply port 20 is stationary in a wall W and is supplied from a stationary hospital infrastructure. It is also possible that the third duct K.3 receives pure oxygen from pressurized cylinders. The supply port 20 preferably provides the pure oxygen at a pressure that is between 2 bar and 8 bar. An optional check valve 29 in the supply line 21 prevents pure oxygen from being forced back into the supply port 20 and into the hospital infrastructure.

A pneumatic pressure reducer 1 comprises an upstream pressure inlet V.3 and a downstream pressure outlet V.2. The upstream pressure inlet V.3 is connected to the supply line 21, the downstream pressure outlet V.2 is connected to the second duct K.2. The pressure reducer 1 reduces the pressure of pure oxygen provided by the supply port 20. Preferably, the pneumatic pressure reducer 1 additionally comprises a control pressure input V.4.

Thus, in the shown embodiment example, two sources provide pure oxygen independently of each other, namely the supply port 20 and the preferably mobile source 25. Thanks to this redundancy, pure oxygen is still available even if one of the two sources 20, 25 fails or is switched off. In the shown embodiment example, the two sources 20, 25 are arranged outside the ventilator 100.

Figure 2:
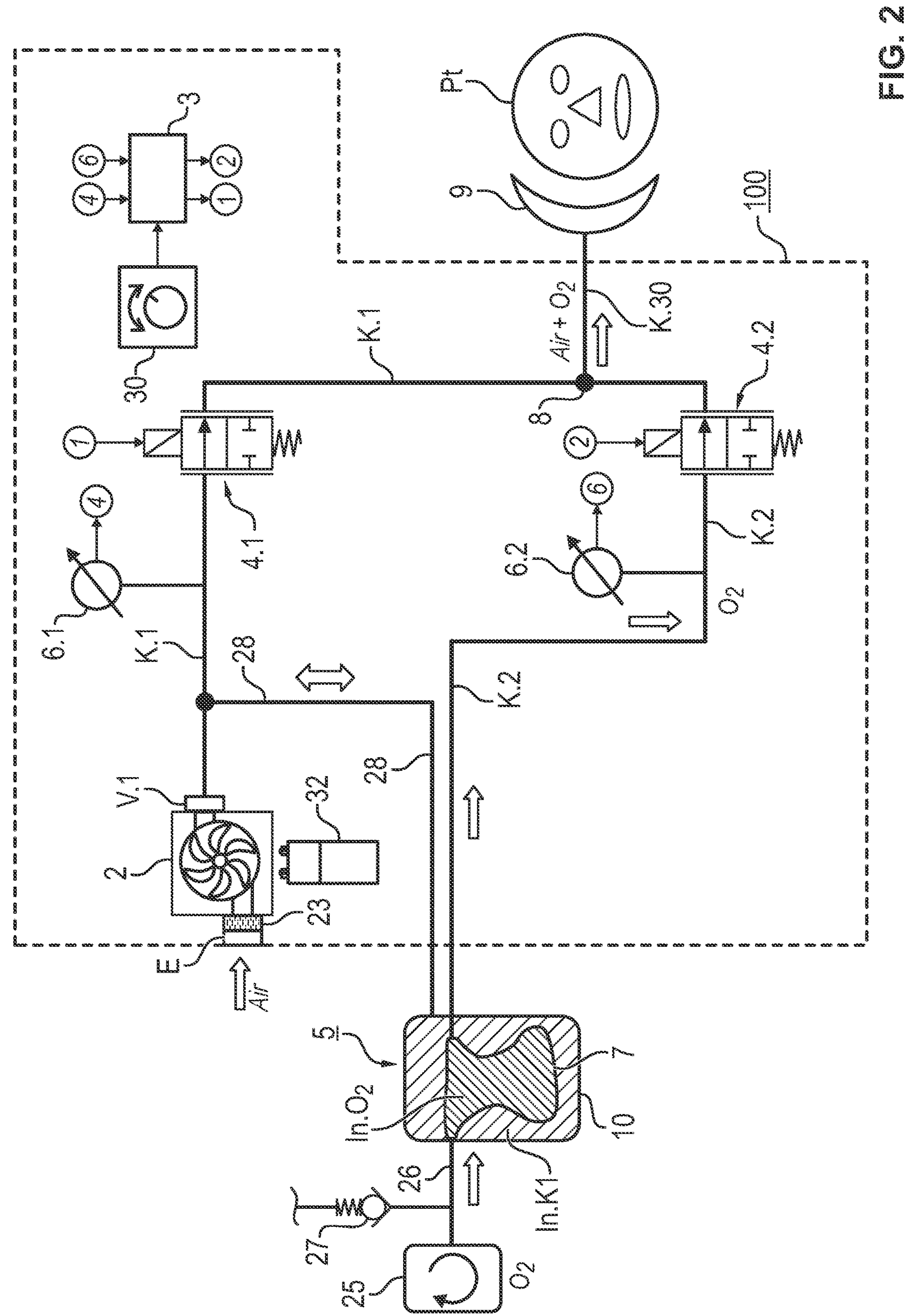
FIG. 2 is a schematic view showing a variation of the embodiment of FIG. 1, wherein a single source provides the pure oxygen.

FIG. 2 schematically illustrates a modification of the ventilator 100 of FIG. 1, with the same reference signs having the same meaning as in FIG. 1.

In this modification, the ventilator 100 has its own power supply unit 32, for example a set of rechargeable batteries (accumulators), the power supply unit 32 in particular driving the blower 2 and providing the electrical energy for the control unit 3, the sensors 6.1, 6.2 and the proportional valves 4.1, 4.2. The ventilator 100 is therefore independent of a stationary power supply network and is used, for example, to provide emergency care to a patient Pt, in particular on board a vehicle or aircraft or at an accident scene. In this embodiment, no stationary supply connection 20 is available. Therefore, no supply line 21 and no pressure reducer 1 and no third duct K.3 and no fourth duct K.4 are required. The second duct K.2 leads from the buffer reservoir 5 to the mixing point 8. Pure oxygen is provided exclusively by the source 25.

Unless otherwise stated, the following description refers to both the embodiment according to FIG. 1 and the embodiment according to FIG. 2.

The pressure in the first duct K.1 may vary with time, including in the section between the supply connection element V.1 and the proportional valve 4.1. In the embodiment example, both the pressure in the second duct K.2 and, in the embodiment according to FIG. 1, the pressure in the third duct K.3 should follow the pressure in the first duct K.1, ideally without time delay. The stationary supply port 20 provides pure oxygen at a pressure that is ideally constant with time. The preferably mobile source 25 also provides pure oxygen, but at a pressure which may be time-varying, the timing of the pressure in the connecting line 26 generally not being synchronized with the pressure in the first duct K.1 and depending, for example, on processes in the source 25. The invention eliminates the need to synchronize the mobile source 25 with the pressure in the first duct K.1 or with the ventilation strokes.

In the following, it is first described how it is achieved that the time course of the pressure in the second duct K.2 follows the time course of the pressure in the first duct K.1. As can be seen in FIG. 1 and FIG. 2, a buffer reservoir 5 is arranged between the outlet of the connecting line 26 and the inlet of the second duct K.2. The terms “inlet” and “outlet” refer to the direction of flow of oxygen to the oxygen mixing point 18 and the mixing point 8, respectively. In the embodiment example, this buffer reservoir 5 is arranged outside the ventilator 100 and can be detachably connected to the ventilator 100. It may instead be a component of the ventilator 100.

The buffer reservoir 5 comprises a rigid housing 10 and a flexible fluid-tight separating element 7, 7.1 arranged entirely inside the housing 10. The separating element 7, 7.1 divides the interior of the housing 10 fluid-tightly into two chambers, namely a supply chamber In.O2 and a control chamber In.K1. Both chambers In.O2, In.K1 are sealed fluid-tightly from the environment, to which the housing 10 contributes.

The connecting line 26 passes through an inlet-side opening in the housing 10, and the second duct K.2 passes through an outlet-side opening in the housing 10. The supply chamber In.O2 is in fluid communication with the connecting line 26 on the inlet side, and in supply fluid communication with the second duct K.2 on the outlet side. Preferably, the connecting line 26 and the second duct K.2 are fluid-tightly connected or connectable to the housing 10. In one embodiment, the supply fluid connection is made through an opening in the housing 10, the second duct K.2 being fluid-tightly connected to this opening.

A pneumatic control line 28 is mechanically connected to the housing 10 and establishes a control fluid connection between that section of the first duct K.1 which leads from the supply connection element V.1 to the proportional valve 4.1 and the control chamber In.K1.

Thanks to the pneumatic control line 28, the pressure in the control chamber In.K1 follows the time-varying pressure in the first duct K.1. Because the separating element 7, 7.1 is fluid-tight and flexible, the pressure in the supply chamber In.O2 follows the time-varying pressure in the control chamber In.K1, at least as long as the pressures in the two chambers In.O2, In.K1 do not differ from each other by more than a design tolerance. Conversely, the pressure in the supply chamber In.O2 may have a feedback effect on the pressure in the first duct K.1 via the internal chamber In.K1 and the control line 28. Ideally, the pressure in the first duct K.1, the pressure in the pneumatic control line 28, in the control chamber In.K1, the pressure in the supply chamber In.O2 and the pressure in the second duct K.2 have the same time course. In practice, unavoidable delays occur, inter alia because of unavoidable leaks and sometimes turbulence. Moreover, inevitably the two chambers In.O2, In.K1 in the housing 10 have only a certain volume each and can compensate pressure differences only up to a certain degree.

In the embodiment according to FIG. 1, a further pneumatic control line 28.1 establishes a further control fluid connection between the first duct K.1 and the control pressure input of the pressure reducer 1. In a first embodiment, this further pneumatic control line 28.1 is directly connected to the first duct K.1, and in a second embodiment, it is connected to the pneumatic control line 28. Thanks to this further pneumatic control line 28.1, the pressure at the downstream pressure outlet V.2 of the pressure reducer 1 follows the pressure in the first duct K.1. Thanks to the further pneumatic control line 28.1, it is not necessary for the control unit 3 to control the pressure reducer 1 or the source 20. Rather, the pressure reducer 1 may be configured as a purely pneumatic and mechanical component.

In the form of realization shown in FIG. 1, FIG. 2, FIG. 4 and FIG. 5, this separating element 7, 7.1 is configured as a flexible bag 7. In another realization form, the separating element 7, 7.1 is configured as a membrane 7.1, cf. FIG. 6. The following description refers to a bag 7 as the separating element. In the described realization form, the supply chamber In.O2 is formed inside the bag 7 and the control chamber In.K1 is formed in the area inside the housing 10 and outside the bag 7. The control chamber In.K1 preferably completely surrounds the bag 7. The bag 7 prevents a fluid connection between the source 25 and the first duct K.1.

If the pressure at which the second source 25 feeds pure oxygen into the connecting line 26 is currently greater than the pressure in the bag 7, the bag 7 is stretched and thereby expanded against the pressure in the control chamber In.K1. Conversely, if the pressure of the source 25 is currently less than the pressure in the control chamber In.K1, the pressure in the control chamber In.K1 compresses the bag 7.

Two adverse events may occur, but should be avoided as much as possible:

- The source 25 supplies too little pure oxygen to the bag 7 (too low volume flow). As a result, the pressure in the control chamber In.K1 compresses the bag 7 completely.
- The source 25 supplies too much pure oxygen to the bag 7 (too high volume flow). As a result, the bag 7 is strongly stretched against the pressure in the control chamber In.K1 and is pressed against the housing 10 from the inside.

In one embodiment, the housing 10 is transparent, or a window is recessed into the housing 10. A user can visually inspect the bag 7 from the outside, and in particular determine whether the bag 7 is fully compressed or else pressed against the housing 10 from the inside.

In another embodiment, a sensor, for example a contact switch, is able to detect the undesired event and report that the bag 7 is pressed against the housing 10 from the inside. Furthermore, in one embodiment, the volume flow sensor 6.2 generates a message when the volume flow through the second duct K.2 is too low. Such a too low volume flow may be caused by the source 25 providing too little pure oxygen.

In another embodiment, a pressure sensor 16.1 measures the pressure in the pneumatic control line 28. This pressure ideally coincides with the pressure in the control chamber In.K1. Another pressure sensor 16.2 measures the pressure in the second duct K.2. This pressure ideally coincides with the pressure in the supply chamber In.O2. If the difference between the pressure in the control chamber In.K1 and the pressure in the supply chamber In.O2 is above a predetermined upper limit, the undesired event may have occurred that the bag 7 is pressed against the housing 10 from the inside. If this pressure difference is below a predetermined lower limit, the undesired event may have occurred that the bag 7 is strongly or even completely compressed. If one of these events has occurred, then a message is preferably generated and output in a form that can be perceived by a human.

Figure 4:
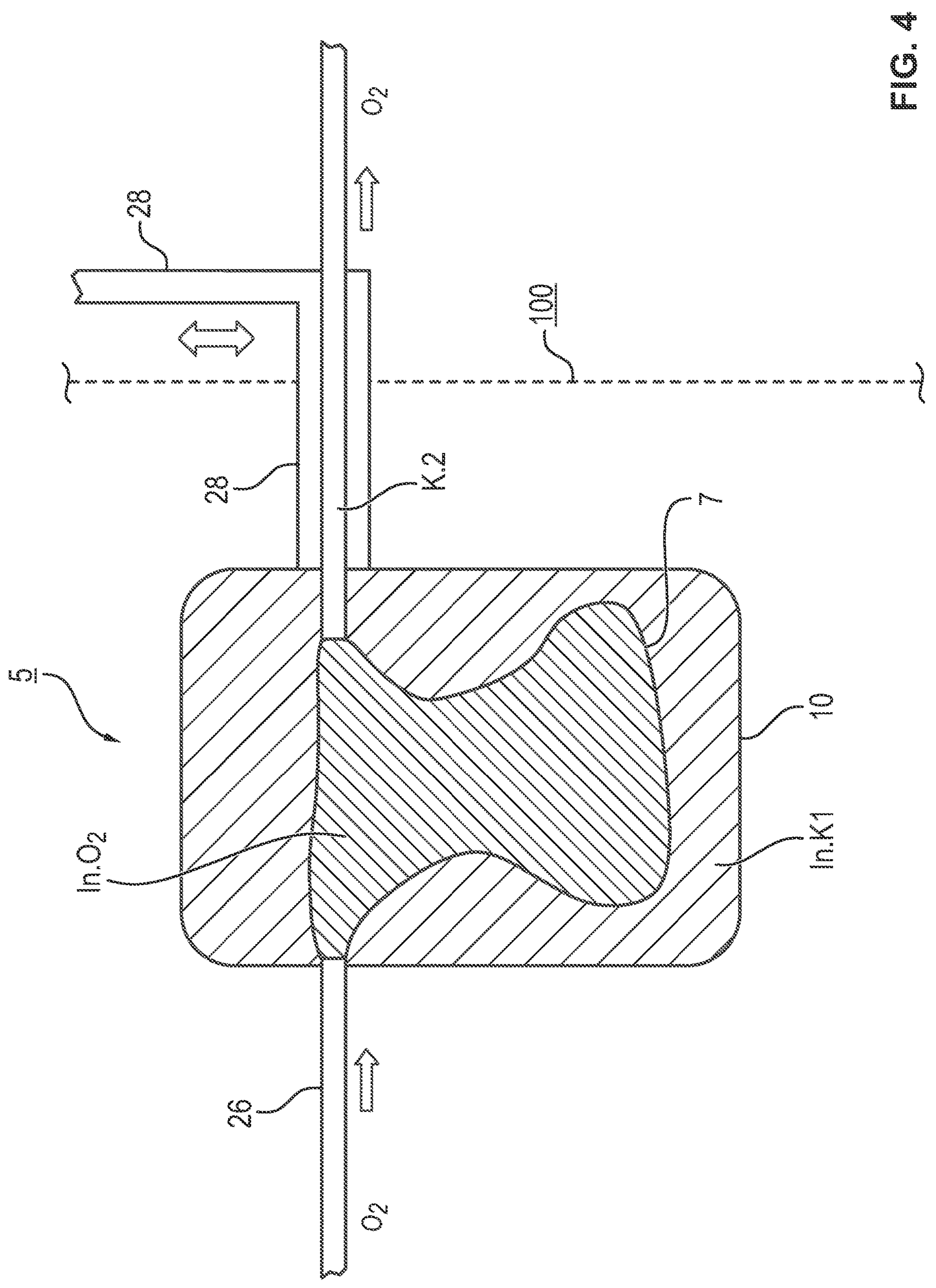
FIG. 4 is a schematic view showing an exemplary coupling of a buffer reservoir with a bag to the ventilator.
Figure 5:
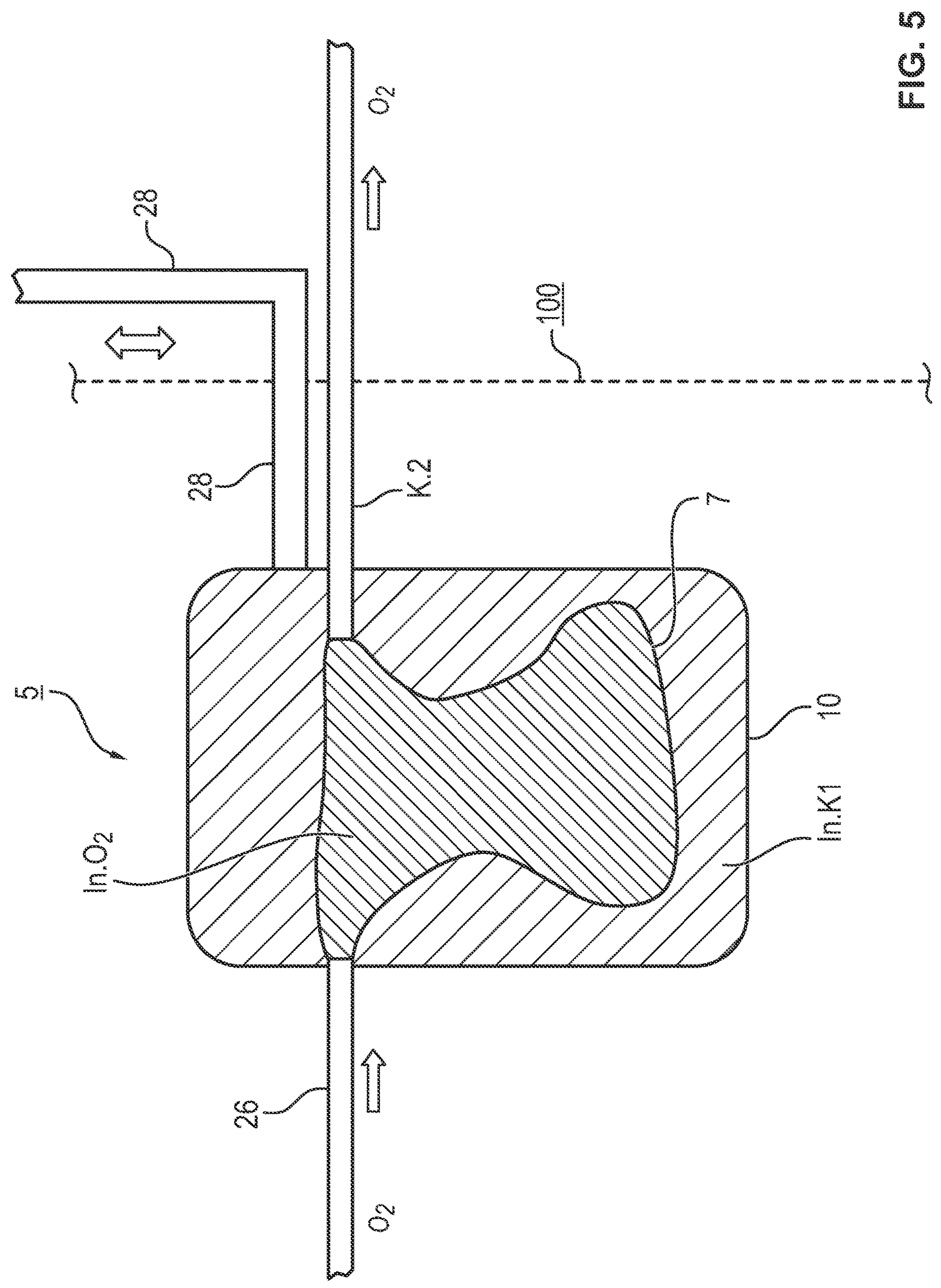
FIG. 5 is a schematic view showing another exemplary coupling of a buffer reservoir with a bag to the ventilator.

In one embodiment, the buffer reservoir 5 is an integral part of the ventilator 100. In another embodiment, the buffer reservoir 5 can be detachably connected to the ventilator 100. FIG. 4 and FIG. 5 show two possible implementations of how the buffer reservoir 5 is detachably connected to the ventilator 100 from the outside. The same reference signs again have the same meaning as in FIG. 1 and FIG. 2.

In the embodiment shown in FIG. 4, a section of the second duct K.2 passes coaxially through the interior of a section of the pneumatic control line 28. Therefore, the buffer reservoir 5 can be connected to the ventilator 100 at a single pneumatic coupling point. It is also possible that the section of the pneumatic control line 28 passes through the interior of the section of the second duct K.2.

In the embodiment according to FIG. 5, two spatially separated pneumatic coupling points are present between the buffer reservoir 5 and the ventilator 100, namely a first coupling point for the second duct K.2 and a second coupling point for the pneumatic control line 28. Preferably, these two coupling points are mechanically different from each other so that a mechanical coding is provided. This mechanical coding prevents the buffer reservoir 5 from being incorrectly connected to the ventilator 100.

In the implementation form just described, the supply chamber In.O2 is formed inside the bag 7 and the control chamber In.K1 surrounds the bag 7. It is also possible that, conversely, the control chamber In.K1 is formed inside the bag 7 and the supply chamber In.O2 surrounds the bag 7.

Figure 6:
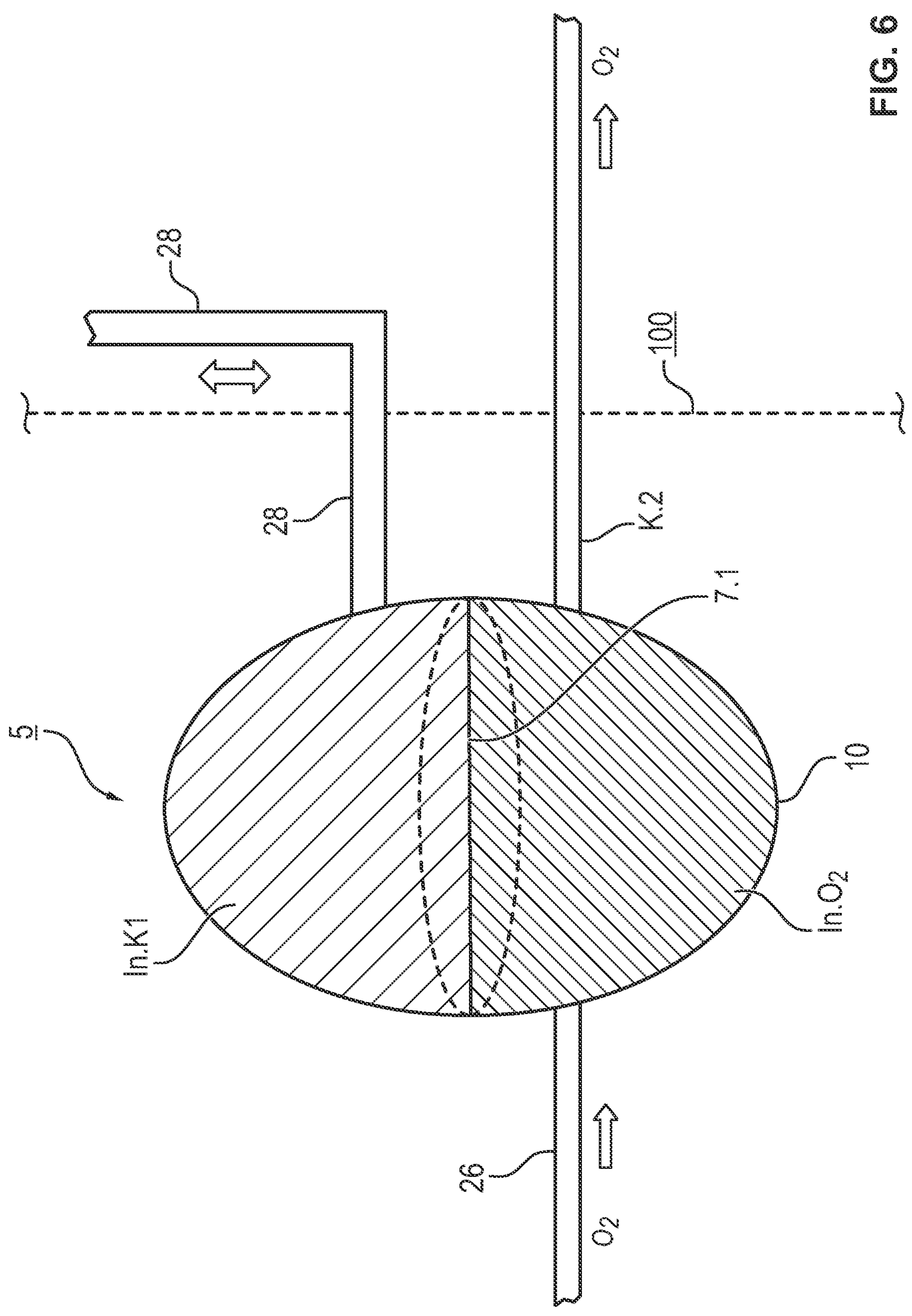
FIG. 6 is a schematic view showing an exemplary coupling of a buffer reservoir with a membrane to the ventilator.

FIG. 6 shows an alternative configuration of the separating element. Instead of a bag 7, a flexible membrane 7.1 is fixed inside the housing 10. This membrane 7.1 divides the interior space in the housing 10 into the supply chamber In.O2 (in FIG. 6 below) and the control chamber In.K1 (in FIG. 6 above). The dashed lines indicate two possible deflections of the membrane 7.1 upwards and downwards. It is also possible that the supply chamber In.O2 is at the top and the control chamber In.K1 at the bottom.

While specific embodiments of the invention have been shown and described in detail to illustrate the application of the principles of the invention, it will be understood that the invention may be embodied otherwise without departing from such principles.

LIST OF REFERENCE CHARACTERS

1 Pneumatic pressure reducer in the second duct K.2, includes the upstream pressure input V.3, the downstream pressure output V.2 and the control pressure input V.4

2 Blower of the ventilator 100, is connected to the first duct K.1 via a supply output, to the inlet E, acts as the first source

3 Signal processing control unit, receives measured values from the volume flow sensors 6.1 and 6.2, controls the proportional valves 4.1 and 4.2

4.1 Proportional valve in the first duct K.1, able to change the volume flow through the first duct K.1, controlled by the control unit 3

4.2 Proportional valve in the fourth duct K.4 or in the second duct K.2, able to change the volume flow through the fourth duct K.4 or the second duct K.2, controlled by the control unit 3

5 Buffer reservoir, comprises the bag 7 and the housing 10, forms inside the housing 10 the control chamber In.K1 and the supply chamber In.O2

6.1 Volume flow sensor, provides a measure of the volume flow through the first duct K.1

6.2 Volume flow sensor, provides a measure of the volume flow through the fourth duct K.4 or the second duct K.2

7 Flexible bag inside the buffer reservoir 5, surrounded by the control chamber In.K1, surrounding the supply chamber In.O2, connected to the connecting line 26 and to the second duct K.2

7.1 Flexible membrane inside the buffer reservoir 5, separates the supply chamber In.O2 from the control chamber In.K1

8 Mixing point into which the two ducts K.1 and K.4 or K.2 open out

9 Patient-side coupling unit, connected to inspiration duct K.30

10 Rigid housing of the buffer reservoir 5

16.1 Pressure sensor, measures the pressure in the pneumatic control line 28

16.2 Pressure sensor, measures the pressure in the second duct K.2

18 Mixing point where the second duct K.2 joins the third duct K.3 and where the duct K.4 starts, serves as the further mixing point

20 Stationary supply port in the wall W for pure oxygen, connected to the third duct K.3, acts as an additional source

21 Supply line, leads from the supply port 20 to the upstream pressure inlet V.3 of the pressure reducer 1

23 Filter behind inlet E

25 Mobile source of pure oxygen, connected to the second duct K.2, acts as second source

26 Connecting line from the mobile source 25 to buffer reservoir 5

27 Pressure relief valve in the connecting line 26

28 Pneumatic line, connects the control chamber In.K1 with the first duct K.1

28.1 Further pneumatic control line, connects the first duct K.1 with the control pressure input V.4

29 Check valve in the supply line 21

30 A rotary knob which a user can turn to preset the required percentage of oxygen in the gas mixture delivered to the patient-side coupling unit 9

32 Power supply unit of the ventilator 100

100 Ventilator, generates a gas mixture of breathing air and pure oxygen, artificially ventilates the patient Pt, includes the supply arrangement according to the invention E Inlet for ambient air, acts as first source, connected to blower 2

In.K1 Control chamber inside the housing 10, is in control fluid communication with the first duct K.1 via the control line 28, in one embodiment surrounds the bag 7

In.O2 Supply chamber inside the housing 10, is in fluid communication with the connecting line 26 and in supply fluid communication with the second duct K.2

K.1 First duct, provides breathing air, which is fed by the blower 2

K.2 Second duct, provides pure oxygen at a lower pressure from source 25

K.3 Third duct, provides pure oxygen at a higher pressure from supply port 20, leads to the oxygen mixing point 18

K.4 Fourth duct, directs pure oxygen from the oxygen mixing point 18 to the mixing point 8

K.30 Inspiration duct, directs the gas mixture from the mixing point 8 to the patient-side coupling unit 9

P Pressure, in particular through the inspiration duct K.30 to the patient-side coupling unit 9

Pt Patient, is artificially ventilated by ventilator 100, wears patient-side coupling unit 9

V.1 Supply connection element of the first duct K.1, connected to a supply output of the blower 2

V.2 Downstream pressure output of pressure reducer 1, connected to second duct K.2

V.3 Upstream pressure inlet of pressure reducer 1, connected to supply line 21

V.4 Control pressure input of pressure reducer 1, connected to the further pneumatic control line 28.1

Vol' Volume flow through inspiration duct K.30 to patient-side coupling unit 9

W Wall, has the supply connection 20 for pure oxygen

What is claimed is:

1. An arrangement for supplying a patient-side coupling unit with a gas mixture, the gas mixture comprising a first gas component and a second gas component, wherein the patient-side coupling unit is configured to be connected to a patient, the supply arrangement comprising:

a first duct with a supply connection element, the supply connection element is configured to establish a fluid connection with a first source for the first gas component;

a second duct;

a mixing point connected to the first duct and connected to the second duct, wherein the first duct is configured to guide the first gas component from the supply connection element to the mixing point;

an inspiration duct configured to direct a gas mixture formed in the mixing point to the patient-side coupling unit;

a buffer reservoir with a supply chamber, the supply arrangement is configured to establish a fluid connection from a second source for the second gas component to the supply chamber, wherein a supply fluid connection between the supply chamber and the second duct is established or establishable, wherein the second duct is configured to direct the second gas component from the supply chamber to the mixing point; and a pneumatic control line establishing a control fluid connection between the first duct and the buffer reservoir, wherein the supply arrangement is configured such that the buffer reservoir, the supply fluid connection, and the control fluid connection together effect a pressure balancing between a pressure in the supply chamber, a pressure in the first duct and a pressure in the second duct, wherein the buffer reservoir comprises a housing and a flexible fluid-tight separating element inside the housing, wherein the separating element fluid-tightly divides the interior of the housing into the supply chamber and a control chamber, and the separating element comprises a flexible bag, wherein the control fluid connection pneumatically connects the control chamber to the first duct and causes a pressure balancing between the control chamber and the first duct, wherein an interior space is formed between the housing and the bag, the interior space surrounding the bag, wherein the supply chamber is formed inside the bag and the control chamber is formed in the interior space between the housing and the bag or the control chamber is formed inside the bag and the supply chamber is formed in the interior space between the housing and the bag.

2. A supply arrangement according to claim 1 wherein the supply chamber is formed inside the bag; and both the fluid connection between the supply chamber and the second source and the supply fluid connection are passed through the housing.

3. A supply arrangement according to claim 1 further comprising a sensor arrangement, wherein:

the sensor arrangement is adapted to measure an indicator for a difference between the pressure in the supply chamber and the pressure in the control chamber; and the supply arrangement is configured to generate a message when the measured pressure difference is outside a predetermined range.

4. A supply arrangement according to claim 1, further comprising:

a third duct; and a pressure reducer including an upstream pressure inlet and a downstream pressure outlet, wherein:

a fluid connection is established or establishable between the upstream pressure inlet of the pressure reducer and a further source for the second gas component;

the downstream pressure outlet of the pressure reducer is connected to the third duct;

the third duct is configured to direct the second gas component from the downstream pressure outlet to the mixing point or to a further mixing point;

the further mixing point is in fluid communication with the mixing point and/or with the patient-side coupling unit; and the pressure reducer is configured to provide the second gas component such that a time course of the pressure at the downstream pressure outlet follows a time course of the pressure in the first duct and/or a time course of the pressure in the second duct.

5. A supply arrangement according to claim 4, further comprising a further pneumatic control line, wherein:

the pressure reducer comprises a control pressure input; and the further pneumatic control line establishes a control fluid connection between the first duct and the control pressure input.

6. A system for supplying a patient-side coupling unit with a gas mixture, the gas mixture comprising a first gas component and a second gas component, the supply system comprising:

a first source configured to provide the first gas component;

a second source configured to provide the second gas component; and a supply arrangement comprising:

a first duct with a supply connection element, the supply connection element is configured to establish a fluid connection with the first source for the first gas component;

a second duct;

a mixing point connected to the first duct and connected to the second duct, wherein the first duct is configured to guide the first gas component from the supply connection element to the mixing point;

an inspiration duct configured to direct a gas mixture formed in the mixing point to the patient-side coupling unit;

a buffer reservoir with a supply chamber, wherein the supply chamber is configured to establish a fluid connection with the second source for the second gas component and with a supply fluid connection with the second duct, wherein the second duct is configured to direct the second gas component from the supply chamber to the mixing point; and a pneumatic control line establishing a control fluid connection between the first duct and the buffer reservoir, wherein the supply arrangement is configured such that the buffer reservoir, the supply fluid connection, and the control fluid connection effect a pressure balancing between a pressure in the supply chamber, a pressure in the first duct and a pressure in the second duct, wherein the buffer reservoir comprises a housing and a flexible fluid-tight separating element inside the housing, wherein the separating element fluid-tightly divides the interior of the housing into the supply chamber and a control chamber, and the separating element comprises a flexible bag, wherein the control fluid connection pneumatically connects the control chamber to the first duct and causes a pressure balancing between the control chamber and the first duct wherein an interior space is formed between the housing and the bag, the interior space surrounding the bag, wherein the supply chamber is formed inside the bag and the control chamber is formed in the interior space between the housing and the bag or the control chamber is formed inside the bag and the supply chamber is formed in the interior space between the housing and the bag.

7. A system according to claim 6, further comprising a further source of the second gas component, wherein:

the supply arrangement further comprises a third duct and a pressure reducer, the pressure reducer including an upstream pressure inlet and a downstream pressure outlet, a fluid connection is established or establishable between the upstream pressure inlet of the pressure reducer and the further source of the second gas component;

the downstream pressure outlet of the pressure reducer is connected to the third duct;

the third duct is configured to direct the second gas component from the downstream pressure outlet to the mixing point or to a further mixing point;

the further mixing point is in fluid communication with the mixing point and/or with the patient-side coupling unit; and the pressure reducer is configured to provide the second gas component such that a time course of the pressure at the downstream pressure outlet follows a time course of the pressure in the first duct and/or a time course of the pressure in the second duct.

8. A system according to claim 7, wherein the supply arrangement further comprises a further pneumatic control line;

the pressure reducer comprises a control pressure input; and the further pneumatic control line establishes a control fluid connection between the first duct and the control pressure input.

9. A system according to claim 7, wherein the further source provides the second gas component at a higher pressure than the second source.

10. A system according to claim 6, further comprising:

a fluid delivery unit connected to the supply connection element and being part of the first gas source; and the patient-side coupling unit, wherein the system is configured for artificial ventilation of a patient, wherein the patient-side coupling unit is configured to be connected to the patient; and the fluid delivery unit is configured to deliver the gas mixture supplied by the supply arrangement to the patient-side coupling unit.

11. A system according to claim 6 wherein the supply chamber is formed inside the bag; and both the fluid connection between the supply chamber and the second source and the supply fluid connection are passed through the housing.

12. A system according to claim 6, further comprising a sensor arrangement, wherein:

the sensor arrangement is adapted to measure an indicator for a difference between the pressure in the supply chamber and the pressure in the control chamber; and the supply arrangement is arranged to generate a message when the measured pressure difference is outside a predetermined range.

13. A process for supplying a patient-side coupling unit with a gas mixture comprising a first gas component and a second gas component, wherein the patient-side coupling unit is connected to a patient, the process being carried out with a supply arrangement comprising a first duct with a supply connection element, a second duct, a mixing point, an inspiration duct, a buffer reservoir with a supply chamber and a pneumatic control line, the pneumatic control line establishing a control fluid connection between the first duct and the buffer reservoir and acting on the buffer reservoir, the process comprising the steps of:

providing the first gas component at the supply connection element;

providing the second gas component;

directing the second gas component to the supply chamber such that the second gas component flows into the supply chamber and is guided from the supply chamber into the second duct;

directing the first gas component, in the first duct, from the supply connection element to the mixing point;

directing the second gas component, in the second duct, from the supply chamber to the mixing point;

directing the gas mixture comprising the first gas component and the second gas component from the mixing point through the inspiration duct to the patient-side coupling unit;

with the pneumatic control line acting on the buffer reservoir, effecting a pressure balancing between a pressure in the supply chamber, a pressure in the first duct and a pressure in the second duct; and providing the buffer reservoir such that the buffer reservoir comprises a housing and a flexible fluid tight separating element inside the housing, the separating element fluid tightly dividing the interior of the housing into the supply chamber as a buffer volume and a control chamber as a control volume acting on the buffer volume, wherein the control fluid connection pneumatically connects the control chamber to the first duct and causes a pressure balancing between the control chamber and the first duct, wherein the separating element comprises a flexible bag, wherein an interior space is formed between the housing and the bag, the interior space surrounding the bag;

wherein the supply chamber is formed inside the bag and the control chamber is formed in the interior space between the housing and the bag or the control chamber is formed inside the bag and the supply chamber is formed in the interior space between the housing and the bag.

14. A process according to claim 13, wherein the supply arrangement further comprises a third duct and a pressure reducer including an upstream pressure inlet and a downstream pressure outlet, wherein a fluid connection is established or establishable between the upstream pressure inlet of the pressure reducer and a further source for the second gas component;

wherein the downstream pressure outlet of the pressure reducer is connected to the third duct;

wherein the third duct is configured to direct the second gas component from the downstream pressure outlet to the mixing point or to a further mixing point in fluid communication with the mixing point and/or with the patient-side coupling unit; and wherein the pressure reducer is configured to provide the second gas component such that a time course of the pressure at the downstream pressure outlet follows a time course of the pressure in the first duct and/or a time course of the pressure in the second duct.

15. A process according to claim 13, further comprising:

providing a fluid delivery unit connected to the supply connection element;

connecting the patient-side coupling unit to the patient; and ventilating the patient, wherein the fluid delivery unit is configured to deliver the gas mixture generated by the supply arrangement to the patient-side coupling unit.

* * * * *